US010143833B1

(12) United States Patent
Ochs et al.

(10) Patent No.: US 10,143,833 B1
(45) Date of Patent: Dec. 4, 2018

(54) METHODS OF PAIN AND INFLAMMATION TREATMENT BY DYNAMIC ELECTRIC STIMULATION

(71) Applicant: OCHSLABS, INC., Sebastapol, CA (US)

(72) Inventors: Len Ochs, Sebastapol, CA (US); Catherine Wills, Sebastopol, CA (US)

(73) Assignee: OCHSLABS LLC, Sebastopol, CA (US)

(*) Notice: Subject to any disclaimer, the term of this patent is extended or adjusted under 35 U.S.C. 154(b) by 0 days.

(21) Appl. No.: 15/794,618

(22) Filed: Oct. 26, 2017

Related U.S. Application Data

(60) Provisional application No. 62/413,955, filed on Oct. 27, 2016.

(51) Int. Cl.
| A61N 1/00 | (2006.01) |
| A61N 1/04 | (2006.01) |
| A61B 5/00 | (2006.01) |
| A61N 1/36 | (2006.01) |

(52) U.S. Cl.
CPC .......... A61N 1/0456 (2013.01); A61B 5/6801 (2013.01); A61N 1/36021 (2013.01); A61B 5/4836 (2013.01); A61B 5/7257 (2013.01); A61N 1/36017 (2013.01); A61N 1/36031 (2017.08); A61N 1/36034 (2017.08); A61N 1/36071 (2013.01)

(58) Field of Classification Search
CPC .............. A61N 1/0456; A61N 1/36021; A61N 1/36031; A61N 1/36034; A61N 1/36017; A61N 1/36071; A61B 5/6801; A61B 5/4836; A61B 5/7257
See application file for complete search history.

(56) References Cited

U.S. PATENT DOCUMENTS

| 1,155,036 | A | 9/1915 | Brooks et al. |
| 1,908,688 | A | 5/1933 | Call |
| 4,121,593 | A | 10/1978 | Kastrubin et al. |
| 4,503,863 | A | 5/1985 | Katims |
| 6,662,051 | B1 | 12/2003 | Eraker et al. |
| 8,014,877 | B2 | 9/2011 | Colthurst |
| 8,082,031 | B2 | 12/2011 | Ochs |
| 8,239,014 | B2 | 8/2012 | Ochs |
| 2012/0065538 | A1 | 3/2012 | Friedman |
| 2014/0379045 | A1* | 12/2014 | Rahimi ................... A61N 1/36 607/46 |

* cited by examiner

*Primary Examiner* — George Manuel
(74) *Attorney, Agent, or Firm* — Edward S. Sherman

(57) ABSTRACT

An apparatus is used in a therapeutic process to provide relief of pain and swelling by dynamic electric stimulation at very low power levels at frequencies between about 2 to 100 Hz. in which the stimulation frequency is constantly offset from the detected dominant frequency by between about 2 to 20 Hz. The pain relief benefits can last weeks, even though the treatment duration is generally well under a minute.

13 Claims, 10 Drawing Sheets

100

METHODS OF PAIN AND INFLAMMATION TREATMENT BY DYNAMIC ELECTRIC STIMULATION

CROSS REFERENCE TO RELATED APPLICATIONS

The present application claims the benefit of priority to the US Provisional Patent application of the same title that was filed on Oct. 27, 2016, having application Ser. No. 62/413,955, and is incorporated herein by reference.

BACKGROUND OF INVENTION

The present invention relates to an apparatus and method of muscle and connective tissue therapy and pain relief that deploys dynamic electrical stimulation.

Electrical stimulation is known to reduce or block pain signals conduction in nerves. Transcutaneous electrical nerve stimulation (TENS) has been used to treat pain, and other medical conditions. TENS units are worn almost continuously by the patient, and the technical evolution of these devices is generally disclosed in the following US Patents, which are all incorporated herein by reference:

U.S. Pat. No. 8,014,877 B2 (J. Colthurst) published Sep. 6, 2011

U.S. Pat. No. 6,662,051 B1 (S. Eraker et al.) published Dec. 9, 2003

U.S. Pat. No. 4,503,863 (J. Katims) published May 12, 1985

U.S. Pat. No. 4,121,593 (E. Kastrubin et al.) published Oct. 24, 1978

U.S. Pat. No. 1,908,688 (L. Call) published May 16, 1933

U.S. Pat. No. 1,155,036 (S. Brooks et al.) published Sep. 28, 1915

More recently, it has been suggested that the efficacy of pain treatment with electrical stimulation can be improve by optimizing the local placement of electrode within muscles based muscle electrical activity, from a electromyagram (EMG), as disclosed in the U.S. patent application Ser. No., 2012/0065538 A1 (E. Friedman), which published Mar. 15, 2012, and is incorporated herein by reference. A clinician uses the disclosed device to optimize the placement of embedded needle electrodes from the received EMG signal. The spectrum of signal received at the needle electrodes is filtered to acquire signals only within a diagnostic band of frequencies corresponding to the EMG spectrum, which is generally considered to be from about 100-1500 Hz, and by some to be in more specific frequency bands of about 100-200 Hz. and/or 500-1500 Hz. The applied stimulation signals are described as having amplitude: 0-20 mA, and more preferably 1 mA, which are applied at a frequency: 1, 3, 5, 7 or 10 Hz, with a pulse width between about 50 to 500 microseconds.

While the application goes on to describe that the stimulation parameters can be varied widely, the application does not teach or disclose a means to improve on the major problem of TENS use, which is accommodation, in which stimulated nerves over time accommodate to the electrical impulse, and eventually diminish the effectiveness of blocking pain signal transmission to the brain. In such accommodation, pain relief is typically sacrificed due to the interaction between amplitude and pulse width. As the duration of a pulse is shortened, the amplitude must be increased to maintain the required pain signal blocking effect. Hence, such devices to be effective for long term pain management must be capable of modulating the amplitude and pulse width over long treatment duration. Further, the device could not realistically be used by the typical patients, as it involves insertion of electrode needles sub-dermal, as well as clinical expertise in interpreting the results to revise the stimulation schedule to account for such accommodation.

Hence, it would be a significant advance if improvements to electro-stimulation pain treatment did not require implantation of needle electrodes.

It would also be significant advance to have a method of treatment that did not require constant external stimulation, as well as the implanting of electrodes within muscle or other tissue.

It would also be significant advance to have a method of treatment that relieved pain relatively quickly, without the accommodation to the stimulation signal, and that such treatment lasted a considerable amount of time, at least days to weeks, to preclude accommodation from repeated use of the same stimulation signal.

It is a primary object of the present invention to provide an improved mean for therapeutic healing as well as pain reduction, without the deficiencies associates with TENS and other prior art treatment methods. Such deficiencies include without limitation, considerable clinical expertise in identifying the optimum treatment protocol for a particular condition, and either the external placement or insertion of electrodes below the skin.

It is a further object of the present invention to provide therapeutic benefits beyond mere pain relief.

SUMMARY OF INVENTION

In the present invention, the first object is achieved by a method of dynamic electric stimulation, the method comprising the steps of providing an electrical amplifier in signal communication with a portion of a patient's body, continuously acquiring analog electrical signals from the patient in the electrical amplifier, converting the analog electrical signals to a digital format, performing a Fast Fourier transform to convert the digital electrical signals to a frequency domain, filtering the frequency domain electric signal in the range between 0 Hz. to below 100 Hz, determining a dominant frequency of the acquired over the past period of one second at least as often as $1/16$th of a second, calculating a prospective treatment regimen as often as the dominant frequency is determined, said step of calculating further comprising the step of providing a frequency offset value, calculating a prospective treatment frequency by summing the dominant frequency and frequency offset value.

Another object of the invention is achieved by providing a method for dynamic electric stimulation treatment that further comprises the step of providing an updated frequency stimulation signal at least each time the calculated prospective treatment frequency has changed from a previous value.

Another object of the invention is achieved by providing a method for dynamic electric stimulation treatment wherein the stimulation signal is applied to the same portion of the patient body used in the step of continuously acquiring electrical signals from the patient in the electrical amplifier.

Another object of the invention is achieved by providing a method for dynamic electric stimulation treatment wherein the calculated prospective treatment frequency is not feedback in an amplified form to the same portion of the patient body used in the step of continuously acquiring electrical signals from the patient in the electrical amplifier.

Another object of the invention is achieved by providing a method for dynamic electric stimulation treatment wherein the calculated prospective treatment frequency is feedback in an amplified form to the same portion of the patient body used in the step of continuously acquiring electrical signals from the patient in the electrical amplifier by a method of stimulation selected from the group consisting of magnetic, dielectric, capacitance, solid state, vibratory, or other terminus for the dynamic stimulation signal wires, visual and auditory dynamic stimulation.

Another object of the invention is achieved by providing an apparatus for dynamic electric stimulation treatment, the apparatus comprising a plurality of leads for attachment to the patient, an amplifier in signal communication with said leads, the amplifier, a computing means in signal communication with said amplifier to acquire and process the amplified signal, at least one of the amplifier and computing means having computational means to determine a dominant frequency in the amplified signal, by selected signals in the range of 0 to below 100 Hz.

The above and other objects, effects, features, and advantages of the present invention will become more apparent from the following description of the embodiments thereof taken in conjunction with the accompanying drawings.

BRIEF DESCRIPTION OF THE DRAWINGS

FIGS. 6A and 6B are a plan and side elevation view of a preferred embodiment of the inventive apparatus, whereas FIG. 6C is a schematic illustration of an optional signal acquisition/treatment electrode cable or bundle for connection with the device in FIGS. 6A&B.

DETAILED DESCRIPTION

Figure 1:
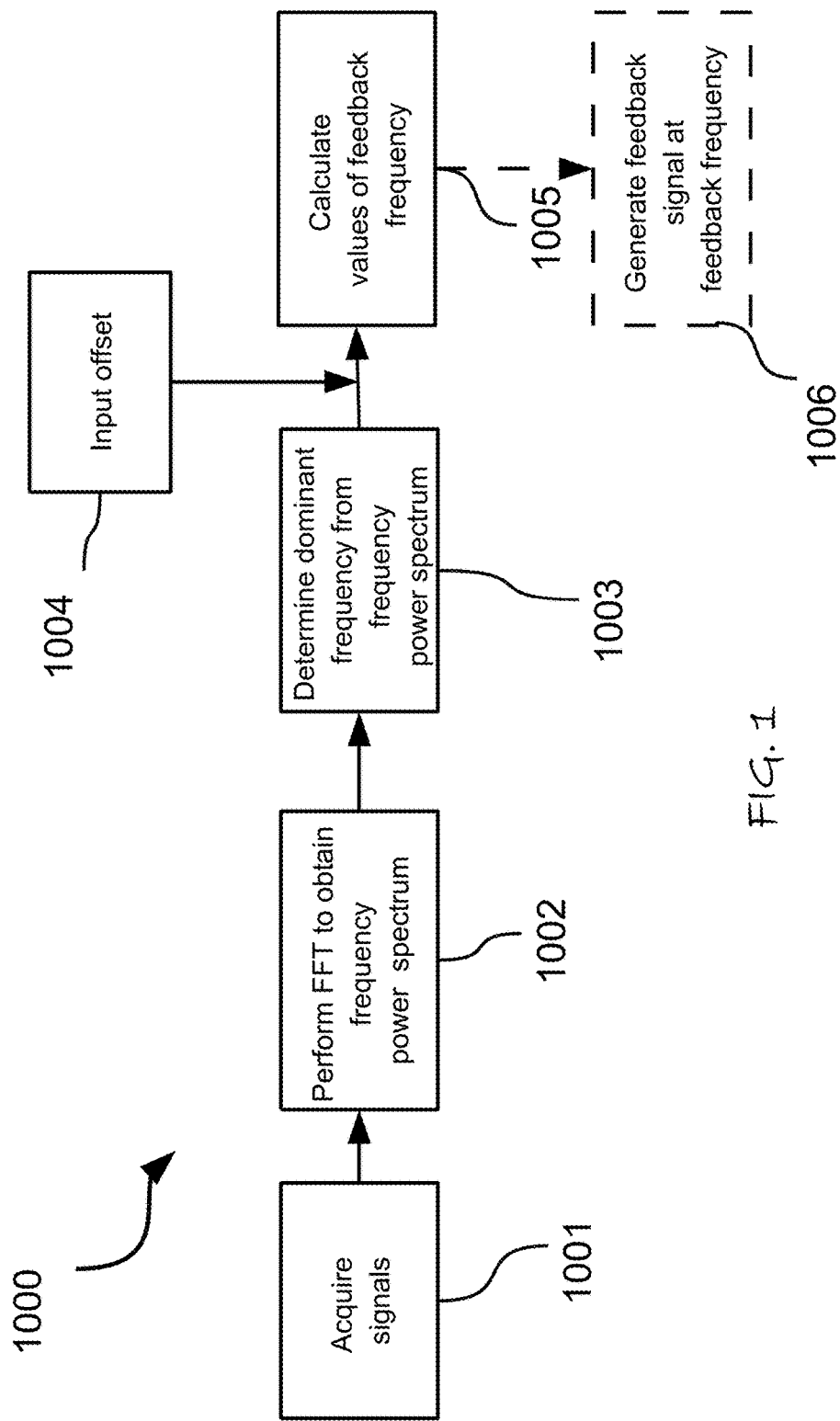
FIG. 1 is a flow chart for the treatment process.

It has been discovered that both pain relief and healing of muscles and other damaged tissues can be obtained by an electric stimulation method and device disclosed herein that differs in form and effect drastically from TENS and prior methods of electrical stimulation therapy.

Such a device and method are illustrated with the aid of FIGS. 1 through 10, wherein like reference numerals refer to like components in the various views, in which the new and improved treatment device generally is denominated 100, as well as a method or process 1000 of operation and use 1000 of the device 100.

Unlike TENS and related electro-stimulation methods, the treatment method deploys very low energy stimulus, and produces long lasting results without the need for constant stimulation, and hence wearing of the device by patients.

The method, more fully disclosed below, involves acquiring electrical signals from the area in which pain or swelling is felt, and using these signals to generate a therapeutic form of electric stimulation. The method does not require a precise placement of either the signal acquiring or the treatment electrodes, which are preferably the same.

In contrast, with TENS the user or clinician selects a fixed frequency and/or wave from and increases power until the pain is relieved, as reported by the patient. The patient may feel a slight vibratory stimulation and involuntary twitches of adjacent muscles in which some current leaks into the neural pathways. The electrical stimulation overwhelms the neural pathways that carry the pain signals, reducing pain.

It has been discovered that pain can be reduced for a longer term without the temporary overwhelming of the associated neural pathways when the electrodes, which are placed proximal to the painful region of a patient, are used to sense signals in the range of 0-60 Hz, well below the EMG signal frequency of at least 100-200 Hz. The electrodes remain connected for some repeated application of energy in the same area of a stimulating signal that is continuously derived from the detected signal. This method will not only relieve pain, but has also been shown to reduce visible swelling and inflammation.

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in block diagram form, rather than in detail, in order to avoid obscuring the present invention.

These embodiments are described in sufficient detail to enable those skilled in the art to practice the invention, and it is to be understood that other embodiments may be utilized and that logical, mechanical, electrical, and other changes may be made without departing from the scope of the present invention.

Some portions of the detailed descriptions that follow may be presented in terms of algorithms and symbolic representations of operations on data bits possibly within a computer memory. These algorithmic descriptions and representations are the means used by those skilled in the data processing arts to most effectively convey the substance of their work to others skilled in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention can be implemented by a computational means that includes any apparatus for performing the operations herein. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, optical disks, compact disk-read only memories (CD-ROMs), and magnetic-optical disks, read-only memories (ROMs), random access memories (RAMs), electrically programmable read-only memories (EPROM)s, electrically erasable programmable read-only memories (EEPROMs), magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor or by any combination of hardware and software. One of skill in the art will immediately appreciate that the invention can be practiced with computer system configurations other than those described below, including hand-held devices, multiprocessor systems, microprocessor-based or programmable consumer electronics, digital signal processing (DSP) devices, network PCs, minicomputers, mainframe computers, and the like.

The invention can also be practiced in distributed computing environments where tasks are performed by remote processing devices that are linked through a communications network. The required structure for a variety of these systems will appear from the description below.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application . . . ), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, or mathematical expression. Thus, one skilled in the art would recognize a block denoting A+B=C as an additive function whose implementation in hardware and/or software would take two inputs (A and B) and produce a summation output (C). Similarly, one skilled in the art would recognize bit notation, such as [D7, . . . , D0] as representing 8 bit locations in a byte with D0 being the least significant bit and D7 being the most significant bit. Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

Figure 4:
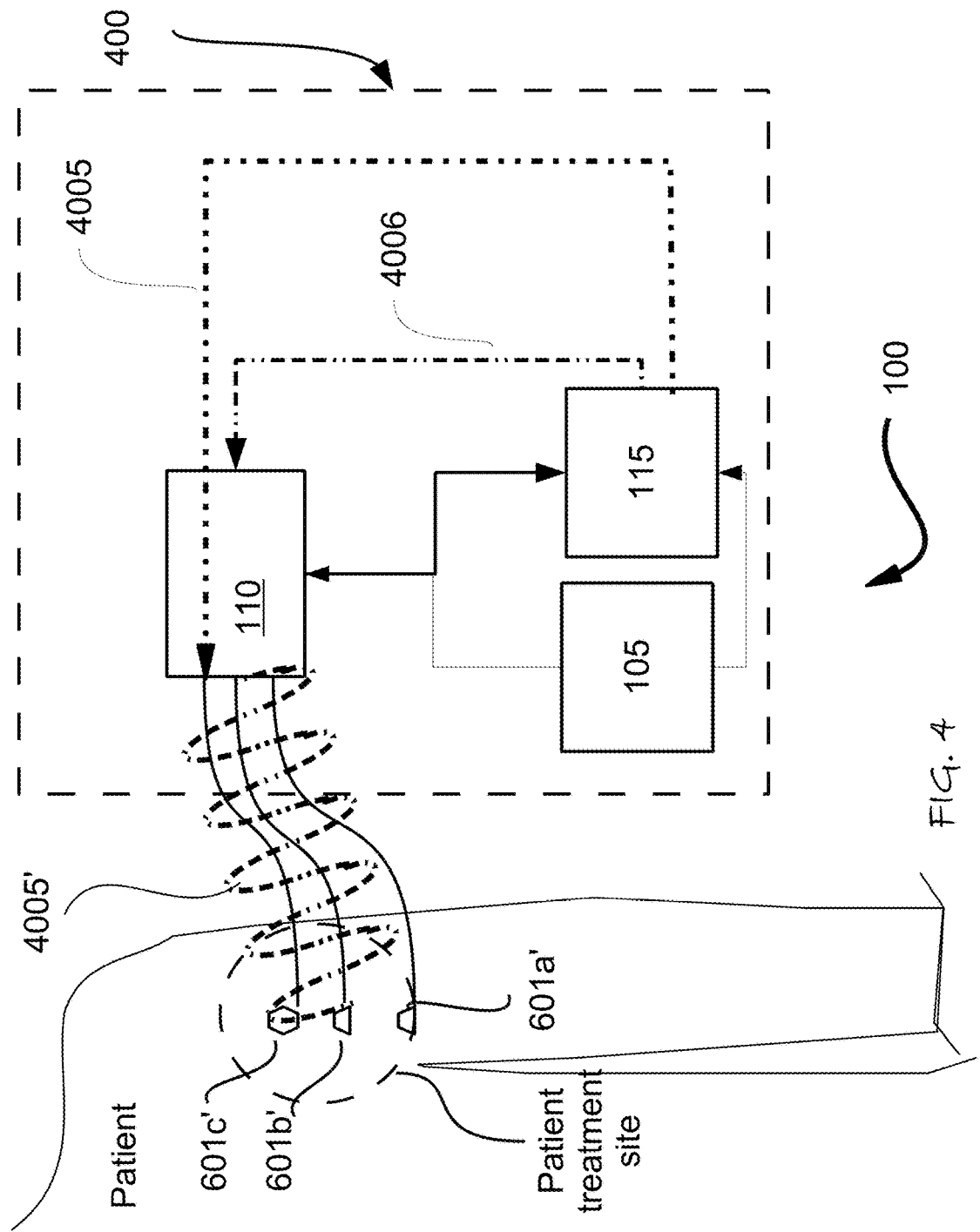
FIG. 4 is schematic diagram illustrating the inventive apparatus in signal communication with the patient in evaluation protocol and dynamic electrical stimulation process for pain and inflammation reduction.
Figure 5:
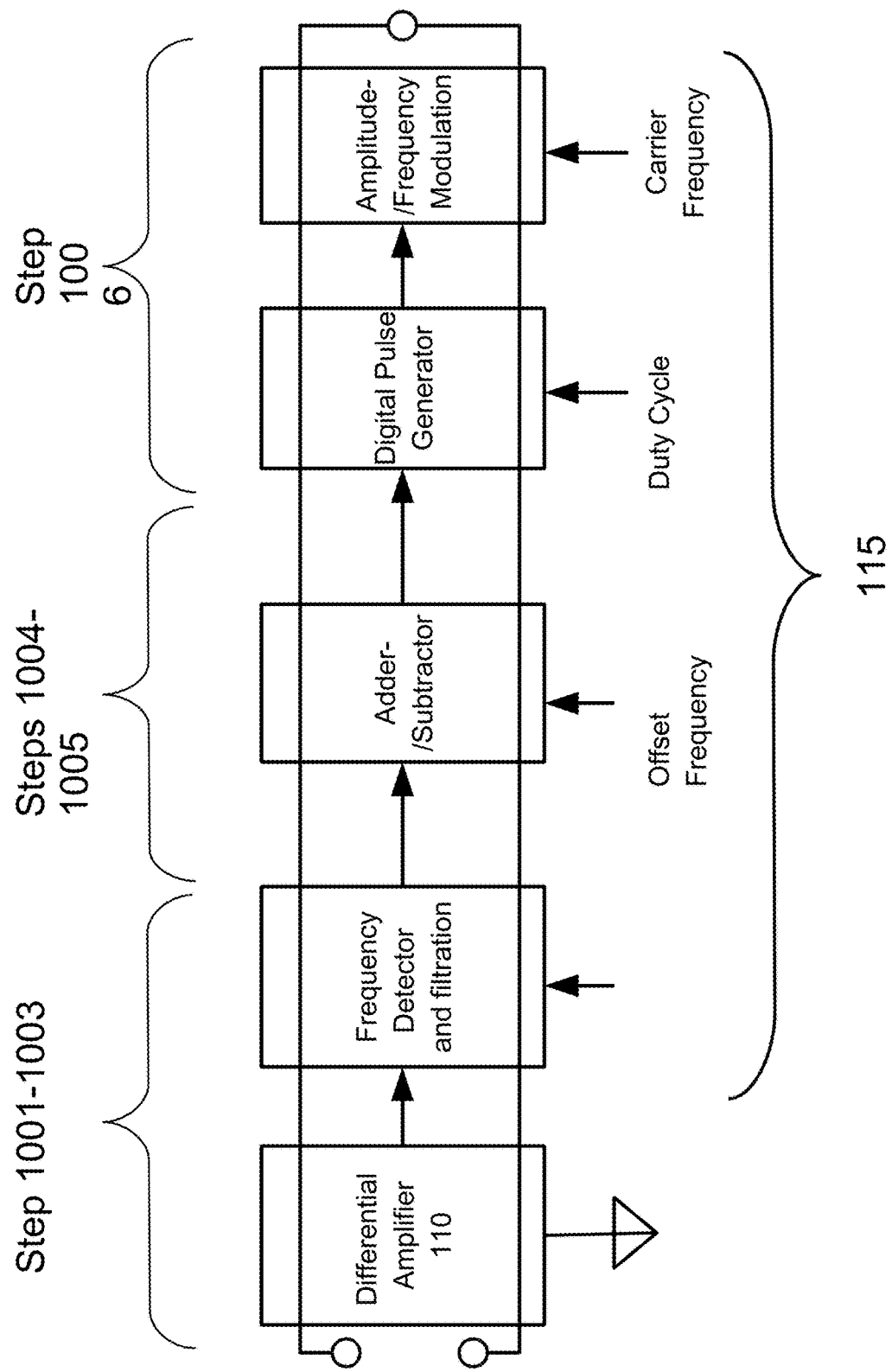
FIG. 5 is a schematic illustration of an amplifier with an embedded microprocessor for optional use in the inventive apparatus.
Figure 6:
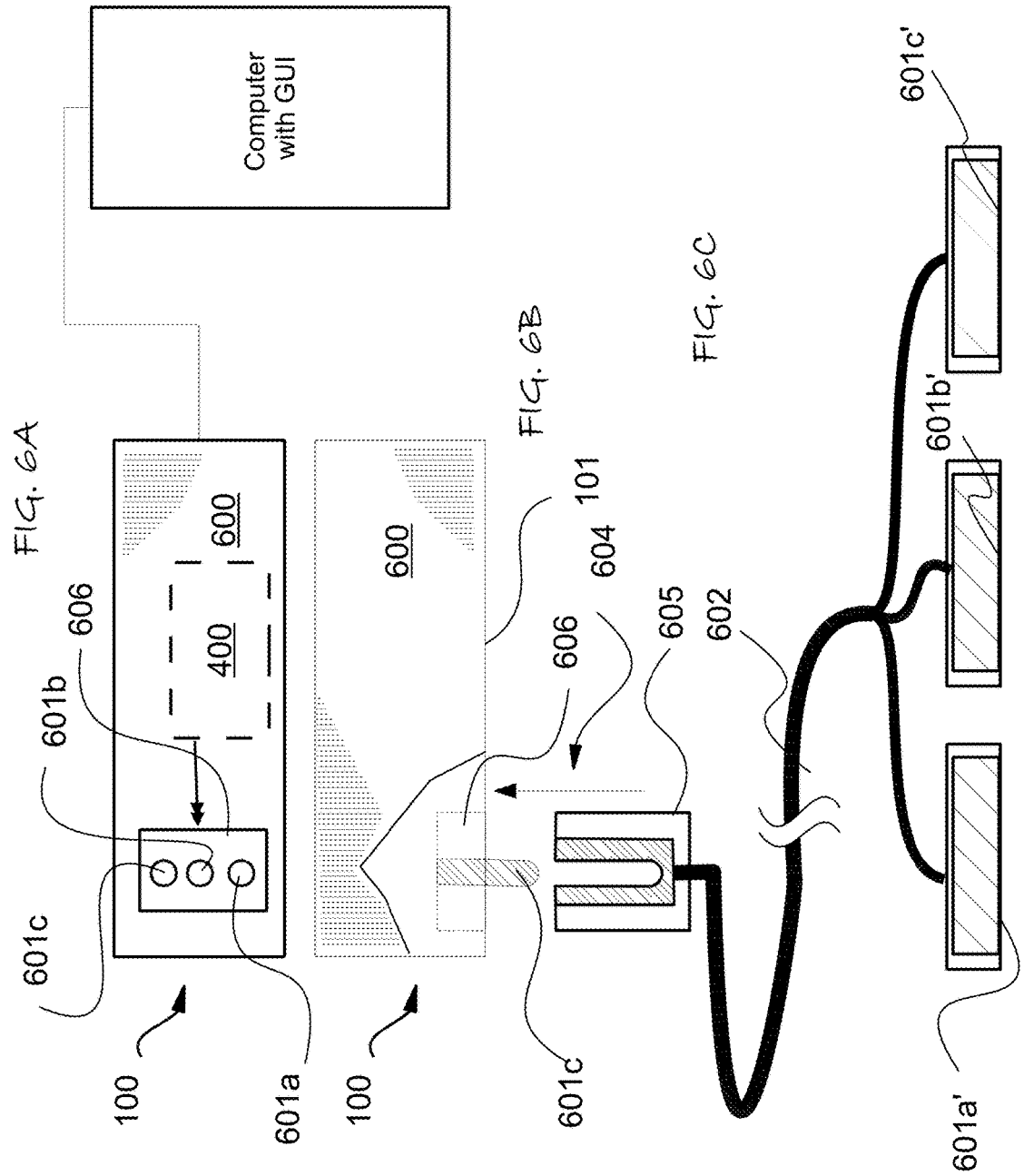

The process of calculating and generating a feedback signal in response to a sensed electrical activity from the patient are illustrated in the flow chart in FIG. 1, which can deploy the apparatus 100 of FIG. 4-6. In the first step 1001 of the treatment process 1000, the electrical activity from electrodes or leads 601 or 601' placed on the skin is acquired as a time domain analog electrical signal. The signal is then digitized and the power spectrum is calculated by a FFT in step 1002 to provide a characteristic spectrum in frequency domain. In the next step, 1003 the dominant frequency of this characteristic spectrum, preferably within the range of 0-60 Hz, is identified. In step 1004 the user is able to select either directly, or through a pre-programmed optional treatment plan, one or more predetermined offset frequency values, typically between about 2 and 20 Hz. In the final step, 1005, the prospective treatment calculated prospective treatment frequency, as referred to herein as "feedback" is calculated as the sum of the predetermined offset frequency and the dominant frequency. The intermediate results of these processes are optionally displayed to the clinician using the equipment, but alternatively can be merely logged in memory of the device, such as for later output or analysis or can be simultaneously output to another data storage source, or a general purpose computer for display on a monitor and/or further processing an analysis. In the an optional step, 1006, the feedback signal is generated and amplified to a higher power for feedback over the same leads 601 or 601' used to acquire the signal, or different output stimuli means described below. However, it has been discovered that in many microprocessor devices, a feedback signal of very low intensity will be generated merely through the calculation process in step 1005.

Figure 2:
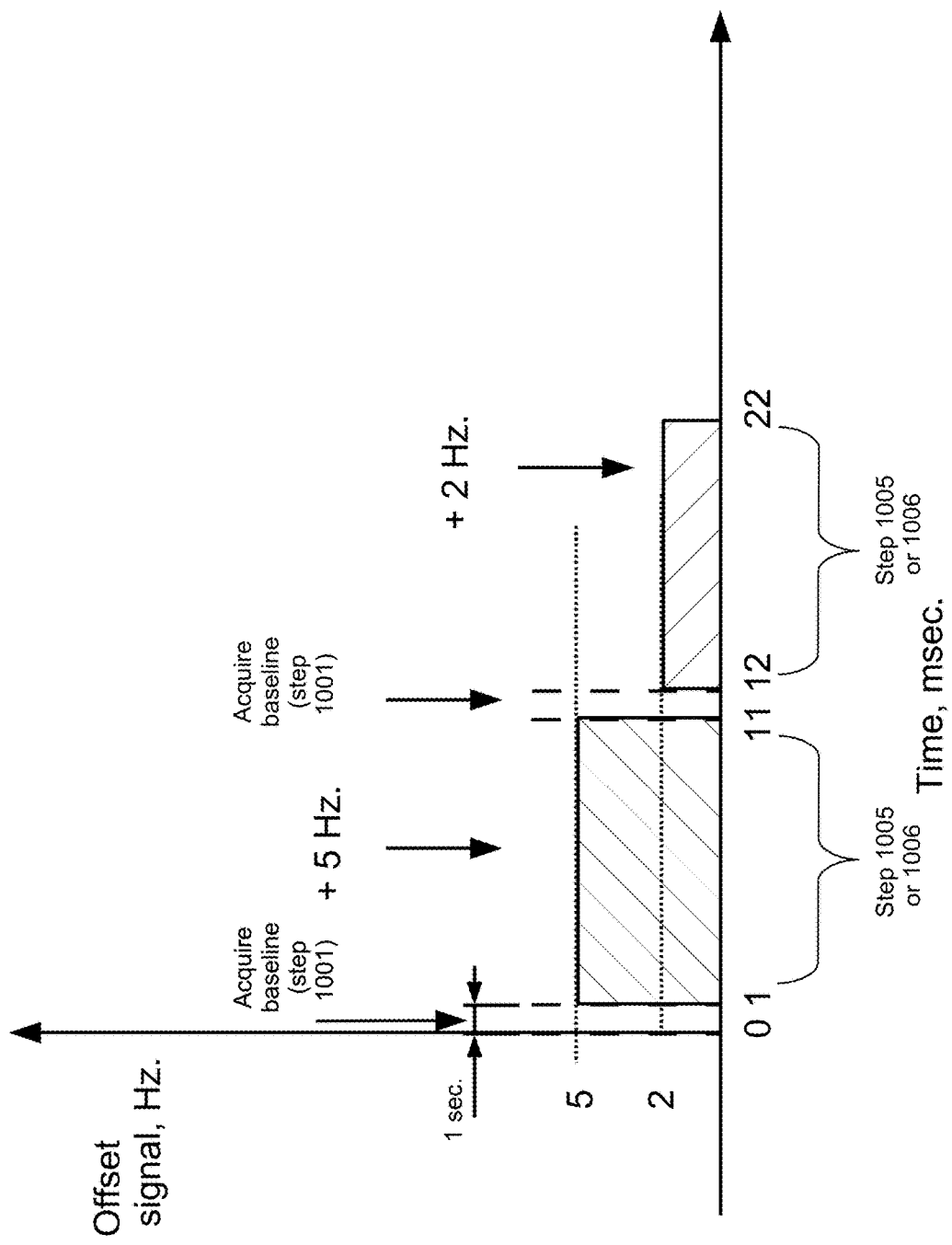
FIG. 2 is a timing diagram of the patient evaluation protocol and dynamic electrical stimulation process for pain and inflammation reduction.

FIG. 2 is a timing diagram of a preferred patient treatment protocol extending from steps 1001 to 1005 or 1006 in FIG. 1. The initial electrical signal or baseline characteristic of the tissue can be acquired (step 1001) for as little as a second. Then the prospective treatment (step 1005 or step 1006) is provided for a total during of 10 sec., during which the calculation and optional display, output or storage of data, are updated every 1/16 sec., per the logic in the flow chart in FIG. 3. However, the update can be more frequent than 1/16, as for example as frequent as every 1/256 sec. It is currently preferred to use an offset value of 2 Hz. for the first 10 sec. treatment duration (elapsed time of 1 to 11 sec.). Preferably, following another 1 second of signal acquisition (between an elapsed time of 11 and 12 seconds) the detected electrical activity from the patient is characterized in the same manner, and a larger offset value is deployed in step 1004. Then the prospective treatment (step 1005 or step 1006) is provided for a total during of another 10 sec. (elapsed time of 12 to 22 sec.) during which the calculation and optional display, output or storage of data, are updated every 1/16 sec., per the logic in the flow chart in FIG. 3. In the second treatment stage the offset is preferably 5 Hz. This process can then be repeated 2 to 6 times.

The dominant frequency is the arithmetic mean of frequency across all values across the entire power spectrum from over a band that is generally less than 100 Hz. Filtering of the signal to use or consider signals in the power spectrum between about zero to below 100 Hz., and more preferably from about zero to 60 Hz., can occur in step 1002 or 1003. The dominant frequency is recalculated each 1/16 of a second from the last 16 measurements. Thus, to the extent that this treatment is changing the characteristic spectrum, the prospective treatment will change during each one second of the treatment period. It should be understood that the result of the calculation is deemed a prospective treatment frequency because there is optionally a further active generation and delivery of a treatment to the patient by the leads 601 or 601'.

Figure 3:
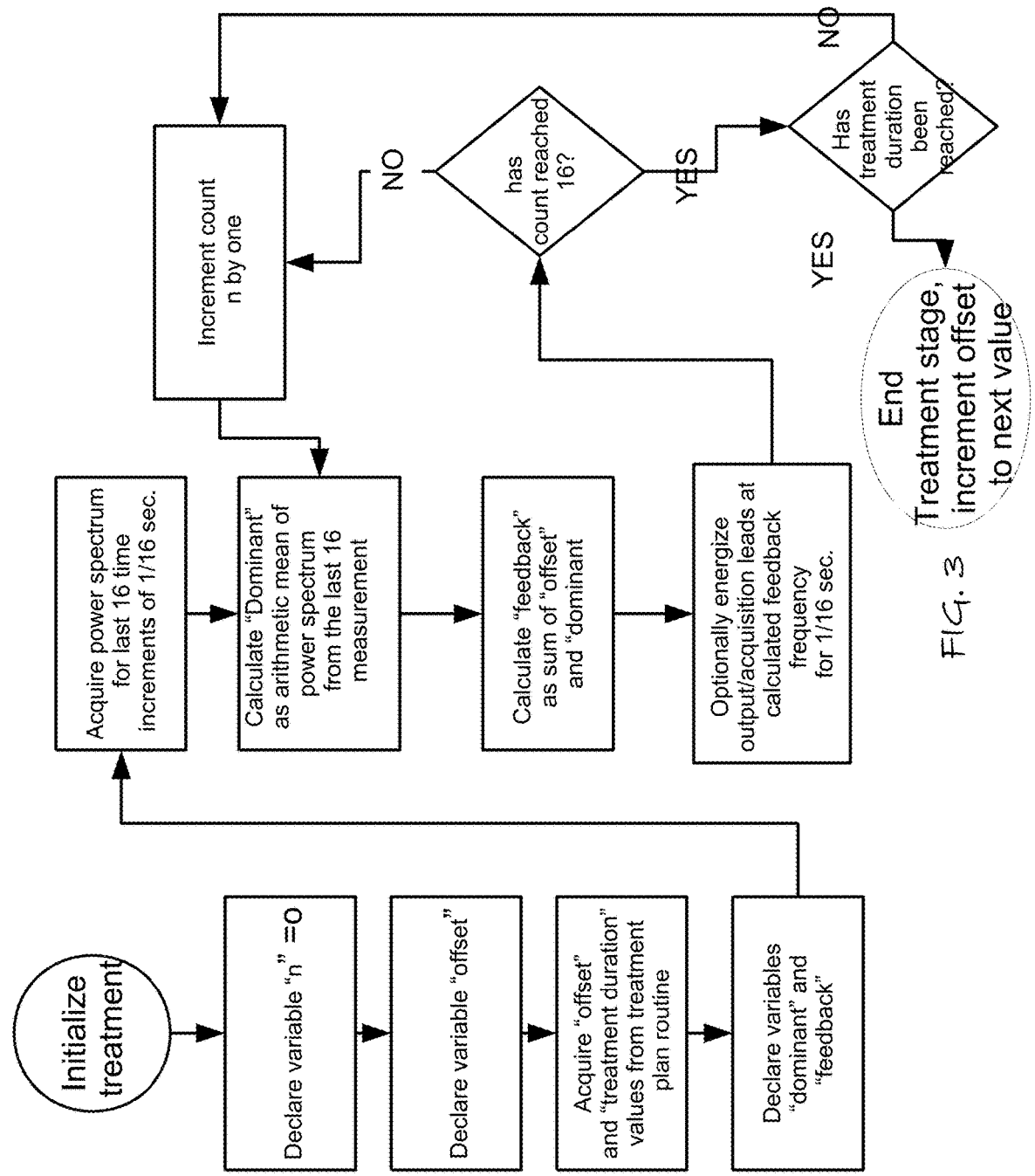
FIG. 3 is a flow chart of the general code deployed in the process illustrated with the flow chart of FIG. 1 and the timing diagram of FIG. 2.

FIG. 3 is a flow chart of the date acquisition and analysis step for a preferred embodiment of the process illustrate in FIG. 1, such as when using the timing sequence of FIG. 2.

Device 100 as shown in FIG. 4 deploys a plurality of leads, 601 or 601', including at least one ground or reference leads in connection a microprocessor 115, which is optionally a digital signal processor, DSP, or comparable device for the signal processing in step 1001 through 1005, a which is optionally connected to an amplifier 110 in signal communication with the signal collection leads 601a and 601b. Preferably lead or electrode 601a is connected to ground, whereas electrode 601b is a reference electrode that with active or powered electrode 601c is placed proximal to the treatment site. The active electrode 601c is optionally powered to provide feedback in step 1006 to the tissue being treated. For examples, it is possible to position reference and ground on ears, and the active electrode on center of pain, or the center of pain can be straddled with all 3 electrodes, as it is not necessarily critical where ground and reference electrodes are placed on the patient. It is has also been discovered that the treatment methods described herein can also be effective even when one or more electrodes 601 or 601'a-c need to be placed on or over a bandage or cast for the greatest proximity to the painful, swollen or injured tissue in the patient.

Figure 10:
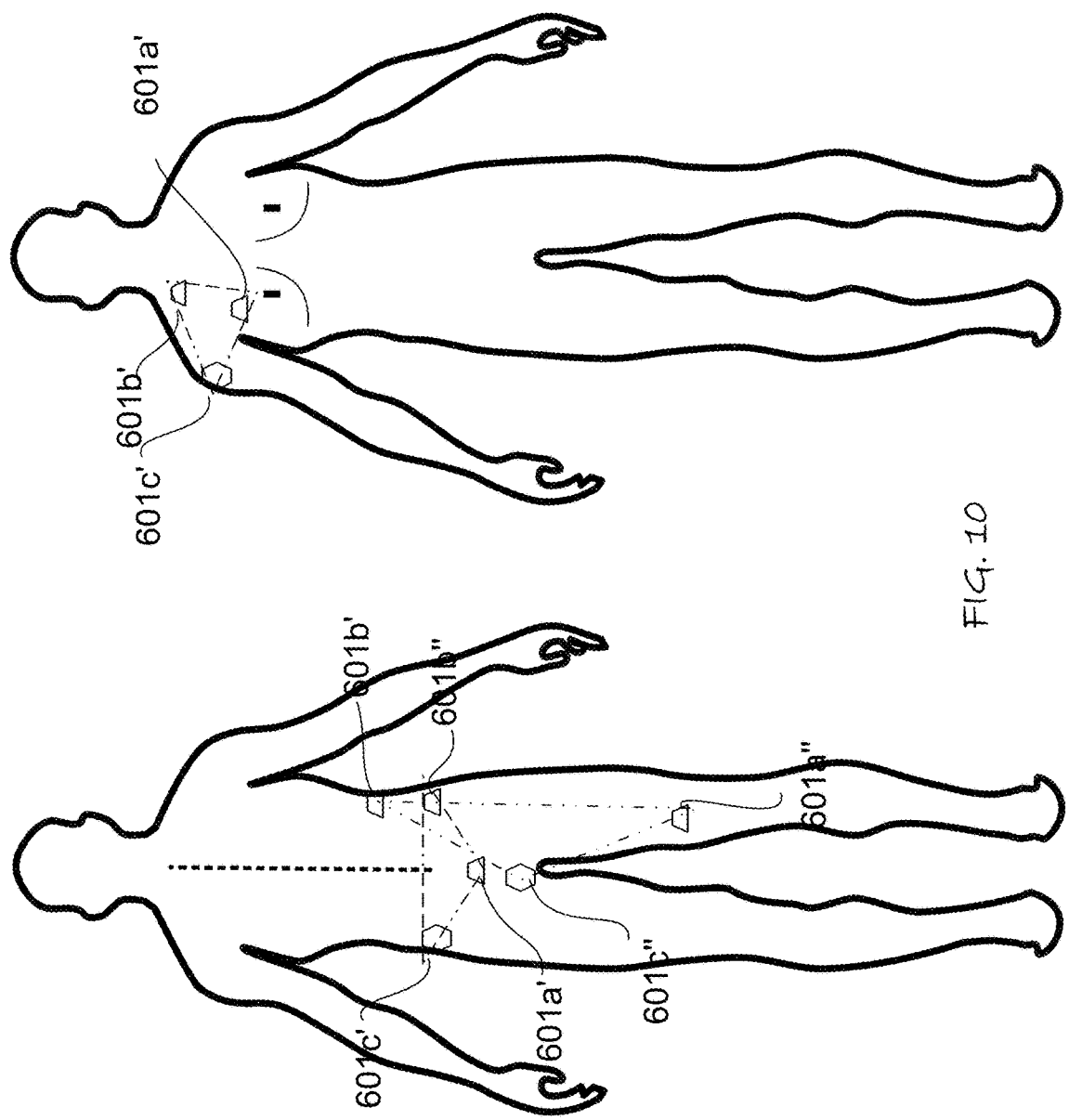
FIG. 10 illustrates alternative placements of electrodes for treating different conditions.

More preferably, the electrodes 601a, 601b and 601c, which will be referred to as an electrode set, are placed on the patient in a manner in which the placement of each electrode defines a corner of a triangular region. The triangular region thus surrounded by the electrode set is preferable specific to the injury or source of pain being treated as follows. FIG. 10 illustrate such placements of the electrode set and the triangular region, in which the right side of the Figure is the front of a patient, and the left side is the rear view of the patient. In the front view the electrodes 601'a-601'c are placed to treat shoulder pain, while in the rear view the same electrodes are shown as placed in a triangle to treat low back pain. An alternative arrange of electrode 601"a-601"c is shown on the right leg and hip as it may be used to treat sciatica that extends into the right leg above the right knee.

In the case of pain and/or swelling of a muscle or muscle group the electrode set is preferably deployed adjacent to where a ligament attaches to opposing ends or sides of the effected muscle just beyond the tendon. The third electrode of the set is then placed beyond the other two electrodes such that the reported pain is within this triangular region. When a treated muscle or muscle group is close to a joint, an electrode is placed on the other side of the joint.

In the case of joint pain or swelling, the electrode set is placed such that the triangular region encompasses the joint.

In the case of the patient having pain within an entire extremity, such as an arm or leg, the triangular area is larger, preferably having one electrode placed at the spine where the nerve feeding the extremity exits. Another electrode is placed over the iliac area and the third sensor on one of the toes, or just beyond the region on the leg where pain is felt.

In the case of the pain extending beyond the joint into an extremity or the body core, it is preferably to extend on electrode beyond the joint so that the triangular area encompasses both the joint and the adjacent painful area. It is currently believed not to be critical where each of the three electrodes are set in defining the triangular region.

It is currently believed that the unamplified feedback from the microprocessor 115 to the differential amplifier 110 (shown as line 4005 in FIG. 4) will continue as unamplified feedback to the patient as shown by 4005' provides therapeutic benefits. In the alternative, an amplified feedback signal is shown as line 4006, can be applied through one or more of the leads or contacts with the patient, such as leads 601a', 601b' and 601c', but preferably to the single lead 601c or 601c'.

The components of microprocessor 115 associated with generating the dynamic stimulation via leads 601 or 601' are illustrated as a block diagram in FIG. 5 to show an optional configuration of the amplifier 110 and microprocessor 115, which may be integrated into a single device. In the treatment process potential difference between the ground and reference electrode 601a and 601b are used to acquire electrical signals from the patient, this signal is them amplified by the differential amplifier 110 and converted to digital format in microprocessor 115 for further signal processing to provide a feedback signal to the active electrode 601c. The signal processing is a conversion of the time domain signal to a frequency domain signal using a fast Fourier transform (FFT). The dominant signal frequency is determined from the FFT. In one embodiment, the active electrode 601c or 601c' is them powered to provide a periodical signal related to the dominant frequency but offset by a predetermined value to a higher frequency.

In the preferred mode of operation filtering occurs to only consider signals in the range of 0-100 Hz. in determining the dominant frequency. Since the offset frequency will generally be from about 1 to 15 Hz, and more preferably between about 2 and 5 Hz., the feedback signal will generally be at between about 10 to 100 Hz., which is well below the range used for TENS treatments.

Fortuitously, it has also been discovered that a number of commercial EEG amplifiers satisfy the above requirements, and are capable of providing the beneficial treatments when programmed and utilized according to this disclosure. Hence, the electrical amplifier and other components of FIG. 1-5 that is used to acquire the characteristic signal and provide the therapeutic feedback stimulus may be an EEG Amplifier/microprocessor, such as one that can be acquired from J&J Engineering Incorporated, 22797 Holgar Ct. Nebr., Poulsbo, Wash. 98370, such as the microcoded J&J 1-330 C2 EEG, subject to restrictions customary for medical devices. Potential alternatives include the NeuroAmp brand EEG amplifier that is available from EEG Info, 22020 Clarendon St. Suite 305, Woodland Hills, Calif. 91367.

While the preferred embodiment of the device, need not deploy a general purpose computer and display commonly used with EEG feedback systems, alternative embodiment may include one or more of a general purpose computer and display, including hand held and portable computing devices such as Smartphone and the like, and may connect with such devices via a Universal Serial bus (USB), or Firewire® port or wireless communication protocol, such as Bluetooth.

Preferably these components are integrated into a common hand held housing 600 shown in FIGS. 6A and 6B, to facilitate placement of the active lead 601c' or 601c on the portion of the patient's body that is enflamed and or the source of pain. The device 100 of FIG. 6A-C deploys the components described above with respect to FIGS. 4 and 5, as block 400, that is the power source 105, differential amplifier 110 and a microprocessor 115 or general purpose computer in signal connection to the electrical leads 601 or 601', the amplifier 110 being energized by the power supply 105. The device 100 enables two alternative modes for connection of the signal detection/output leads to the patient. Device 100 can be used for hand held application of the electrodes 601a-c to the skin. Alternatively in the second mode, the 3 electrical leads 601a, 601b, and 601c, are in indirect signal communication with the patient via attachment of separate electrode lead wire bundle 602 that terminate with electrode pads 601a-c', which contact the patient instead. The electrode leads wire bundle or cable 602 has an input side 604 in a common connector block 605 that is inserted into the cavity 606 of the device 100 to provide signal connection so that integrated electrodes 601a-c, which extend beyond the frame or exterior 101 of the device 100, making signal communication with remote electrodes 601a-c'. It should be appreciated that bundle 602 can be replaced by 2 or more separate wires or bundles when it is desirable to place at least one of the electrodes pads 601a-c' distal from the other two electrode pads.

Hence, the device 100 can be held by the patient self administration by contact the integrated electrodes 601a-c directly with the skin in the painful or swollen, as well as through bandages or casts. However, for the intended treatment of regions that are harder to reach, common connector block 605 is inserted into cavity 606 such that each electrode 601a-c is connected to a corresponding electrode 601' a-c by the wire bundle 602.

Figure 7:
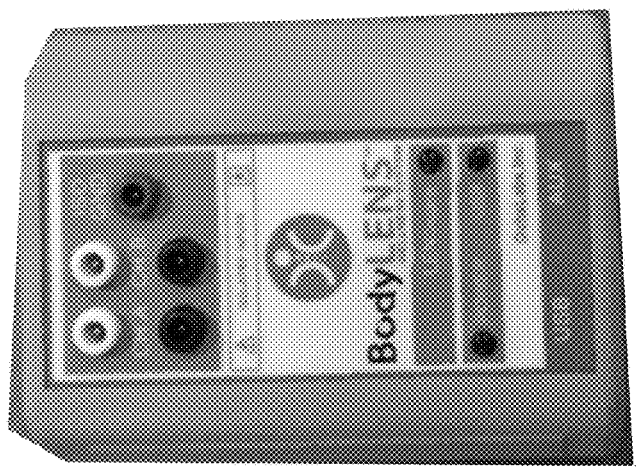
FIG. 7 illustrates an alternative embodiment of the device without leads connected.

FIG. 7 illustrates an alternative embodiment of the device without leads connected. The device of FIG. 7 when connected to a computer having a graphic user interface (GUI) to provide an apparatus for pain treatment, the apparatus comprising a plurality of leads for attachment to the skin of a patient, an amplifier in signal communication with said leads, the amplifier consisting essentially of means to amplify signal received from the leads attached to the patient, a computer in signal communication with said amplifier to acquire and display the aspect of the received signal, at least one of the amplifier and computer comprising computational means to determine the dominant frequency in a lead pair, the computer further comprising: a graphic user interface that provided one of more views of the human body for selected an area to be treated, each area selected being associated with an icon, a user interface for providing a predetermined offset frequency, a computation means to calculate a prospective treatment frequency by summing the predetermined offset frequency and the dominant frequency, wherein the calculated prospective treatment frequency is not feedback in an amplified form to the leads and the computer is operative to log the results of the treatment with each associated icon.

Figure 8:
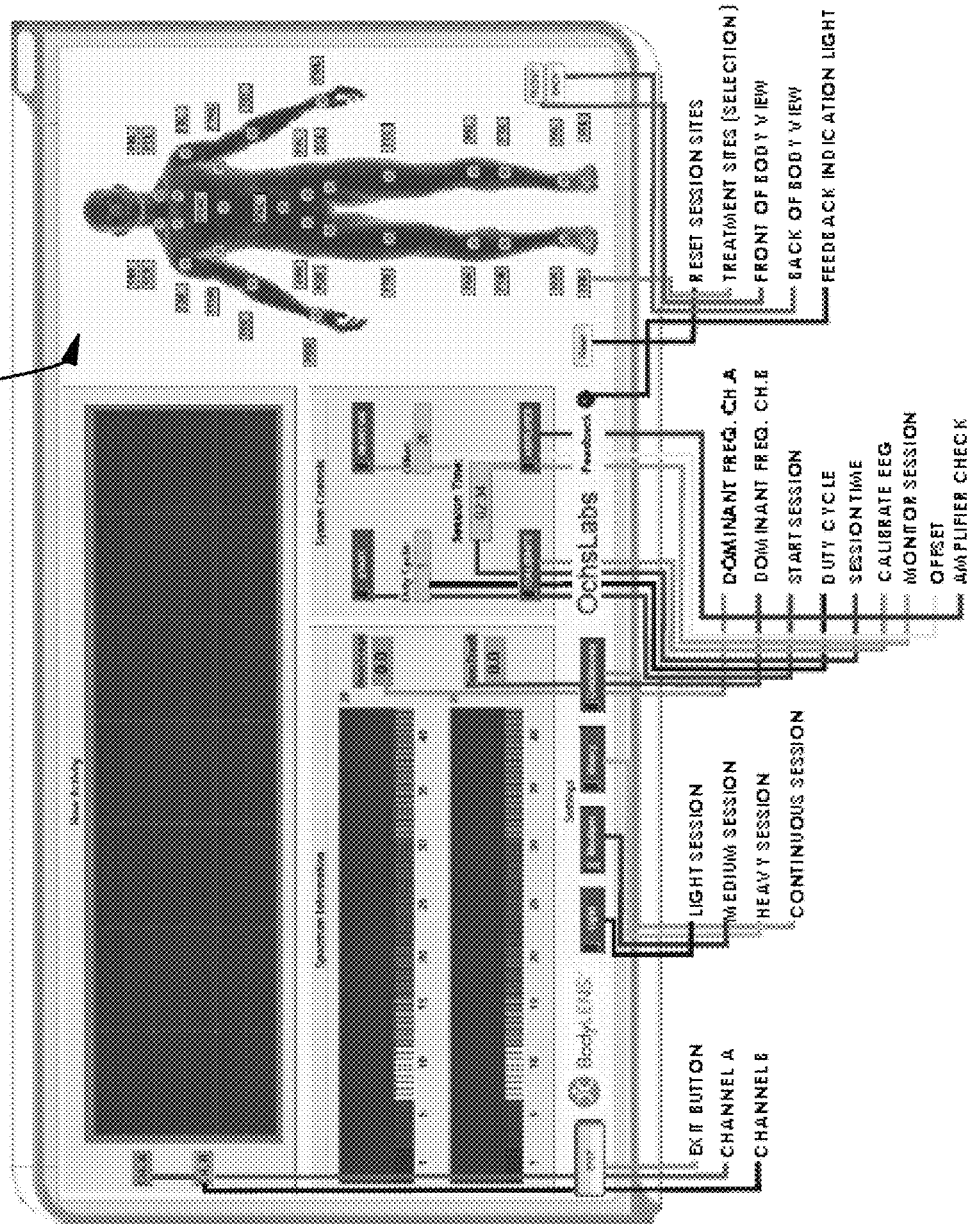
FIG. 8 illustrates a graphic user interface for treatment planning

FIG. 8 illustrates a GUI 801 for treatment planning, of which the use is described in the attached Appendix 1, which is incorporated herein by reference.

The computer and GUI 801 may be used to provide low energy pain management treatment, the method consisting essentially of the steps of providing an amplifier in signal communication with leads, providing a general purpose computer in signal communication with the amplifier to receiver, analyze and display the signals received by the leads and to calculate a prospective treatment regimen, acquiring one or more signals from a patient in the amplifier, converting the analog signals to a digital format, determining the dominant frequency of the signals in the general purpose computer, calculating a prospective treatment regimen in the general purpose computer, said step of calculating further comprising the step of: providing a frequency offset value, calculating a prospective treatment frequency by summing the dominant frequency and frequency offset value, displaying dominant frequency, frequency offset and prospective treatment frequency on the monitor associated with the general purpose computer wherein the general purpose computer has a graphic user interface that is operative to display one or more views of the human body for selected an area to be treated, each area selected being associated with an icon The GUI 801 is used in the process of preparing for treatment by the steps comprising or consisting essentially of providing an amplifier in signal communication with leads, providing a general purpose computer in signal communication with the amplifier to receiver, analyze and display the signals received by the leads and to calculate a prospective treatment regimen, the computer and amplifier being operative to acquire one or more signals from a patient in the amplifier, convert the analog signals to a digital format, determine the dominant frequency of the signals in the general purpose computer, calculate a prospective treatment regimen in the general purpose computer, when said step of calculating further comprises the steps of providing a frequency offset value, calculating a prospective treatment frequency by summing the dominant frequency and frequency offset value, displaying dominant frequency, frequency offset and prospective treatment frequency on the monitor associated with the general purpose computer, wherein the general purpose computer has a graphic user interface that is operative to display one or more views of the human body for selected an area to be treated, each area selected being associated with an icon. The GUI may include references to the portion of the body treated that are logged by the system and used to plan and execute future treatments or extended treatment of multiple regions.

Figure 9:
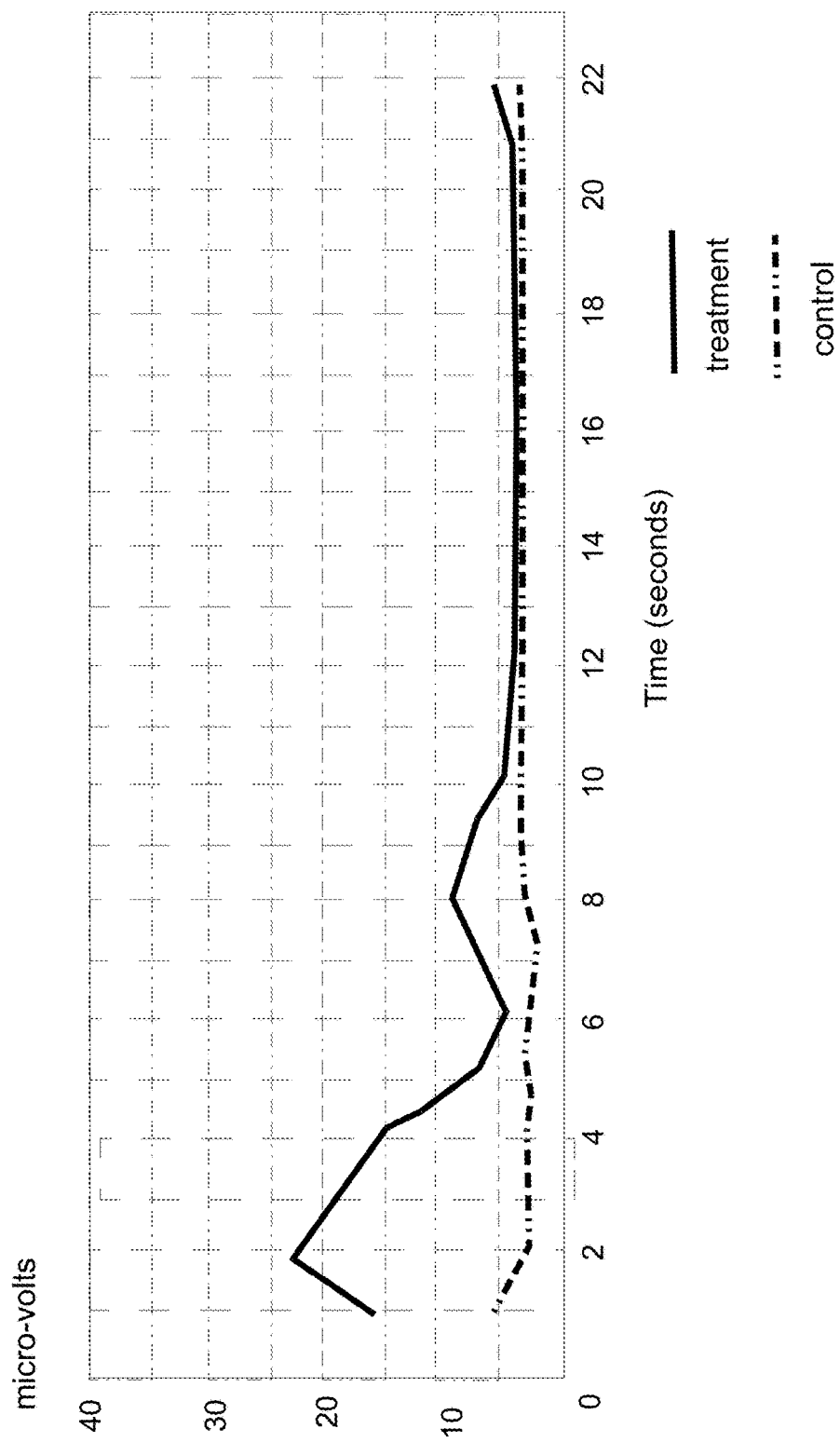
FIG. 9 is plot of the variation of integrated signal during the dynamic electrical stimulation process, which in the "treatment" line resulted in an immediate and dramatic decrease in intensity that occurred as the patient's pain subsided, whereas the "control" signal (of a region not painful) has a much lower intensity and slower decrease of signal.

FIG. 9 is plot of the variation of integrated signal during the dynamic electrical stimulation process, which in the "treatment" line resulted in an immediate and dramatic decrease in intensity that occurred as the patient's pain subsided, whereas the "control" signal (of a region not painful) has a much lower intensity and slower decrease of signal. The -treatment- intensity was measured with the leads surrounding a painful region of the lower back. The -control- intensity was from a nearby non painful region of the back.

No wishing to be bound by theory, it is currently believed that the process of calculation in device 100 generates a very weak feedback of energy back to the microprocessor and on to the patient via the leads 601/601' without further deliberate amplification.

While the method 1000 described above preferably deploys direct contact electrodes 601 or 601', it can alternatively deploy a different transducer to provide dynamic stimulation, including magnetic, dielectric, capacitance, solid state, vibratory, or other terminus for the dynamic stimulation signal wires, including visual and/or auditory dynamic stimulation. Thus, in the preferred method of use, whether the dynamic stimulation signals are amplified or unamplified they can remains at a profoundly low levels of intensity, including sub-threshold of awareness, well under the range of mA and beyond which is frequently used in TENS stimulators.

It is believed the same feedback method can be used with other kinds of stimulation, such as electrical amplifier by a method of stimulation selected from the group consisting of magnetic, dielectric, capacitance, solid state, vibratory, or other terminus for the dynamic stimulation signal wires, visual and auditory dynamic stimulation.

The method disclosed above has successfully treated pain and inflammation in patients elbows, knees, low back, as well as produced rapid reduction in swelling from sports injuries. The treatment has lasted in many patients for 4-8 weeks, before signs of pain return that require re-treatment.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. A method of pain treatment, the method comprising the steps of:
   a) providing an electrical amplifier in signal communication with a portion of a patient's body that is enflamed and/or painful,
   b) continuously acquiring analog electrical signals from the patient in the electrical amplifier,
   c) converting the analog electrical signals to a digital format,
   d) performing a Fast Fourier transform to convert the digital electrical signals to a frequency domain,
   e) filtering the frequency domain electric signal in the range between 0 Hz. to below 100 Hz,
   f) determining a dominant frequency of the acquired over the past period of one second at least as often as $\frac{1}{16}$th of a second,
   g) calculating a prospective treatment regimen as often as the dominant frequency is determined, said step of calculating further comprising the step of:
      i) providing a frequency offset value,
      ii) calculating a prospective treatment frequency by summing the dominant frequency and frequency offset value.

2. The method of pain treatment according to claim 1 further comprising the step of providing an updated frequency stimulation signal at least each time the calculated prospective treatment frequency has changed from a previous value.

3. The method of pain treatment according to claim 2 wherein the stimulation signal is applied to the same portion of the patient body used in the step of continuously acquiring electrical signals from the patient in the electrical amplifier.

4. The method of pain treatment according to claim 3 wherein the calculated prospective treatment frequency is not feedback in an amplified form to the same portion of the patient body used in the step of continuously acquiring electrical signals from the patient in the electrical amplifier.

5. The method of pain treatment according to claim 3 wherein the calculated prospective treatment frequency is feedback in an amplified form to the same portion of the patient body used in the step of continuously acquiring electrical signals from the patient in the electrical amplifier by a method of stimulation selected from the group consisting of magnetic, dielectric, capacitance, solid state, vibratory, or other terminus for the dynamic stimulation signal wires, visual and auditory dynamic stimulation.

6. An apparatus for pain treatment, the apparatus comprising:
   a) a plurality of leads for attachment to the skin of a patient,
   b) an amplifier configured for signal communication with said leads, the amplifier consisting essentially of a means to amplify signals received from the leads attached to the patient,
   c) a computer in signal communication with said amplifier to acquire and display an aspect of the received signal,
   d) at least one of the amplifier and computer comprising computational means to determine a dominant frequency of a lead pair consisting of at least 2 of the plurality of leads,
   e) the computer further comprising:
      i) a graphic user interface that provides one of more views of the human body for selecting an area to be treated, each area selected being associated with an icon,
      ii) a user interface for providing a predetermined frequency offset value,
      iii) a computation means to calculate a prospective treatment frequency by summing the predetermined frequency offset value and the dominant frequency,
      iv) wherein the calculated prospective treatment frequency is not feedback in an amplified form to the leads and the computer is operative to log the results of the treatment with each associated icon.

7. The apparatus for pain treatment according to claim 6 wherein the computation means is operative to:
   a) continuously acquire analog electrical signals from the amplifier,
   c) convert the analog electrical signals to a digital format,
   d) perform a Fast Fourier transform to convert the digital electrical signals to a frequency domain,
   e) filter the frequency domain electric signal in a range between 0 Hz. to below 100 Hz,
   f) determine a dominant frequency of the frequency domain electric signal over the past period of one second at least as often as $\frac{1}{16}$th of a second.

8. The apparatus for pain treatment according to claim 7 wherein the computation means is further operative to calculate a prospective treatment regimen as often as the dominant frequency is determined.

9. The apparatus for pain treatment according to claim 6 wherein the amplifier is operative to continuously acquire analog electrical signals from a patient and the computation means is further operative to:
   a. convert the analog electrical signals to a digital format,
   b. perform a Fast Fourier transform to convert the digital electrical signals to a frequency domain,
   c. filter the frequency domain electric signals in a range between 0 Hz. to below 100 Hz, d. determine a dominant frequency of the filtered frequency domain electric signals over the past period of one second at least as often as $\frac{1}{16}$th of a second, and
e. calculate a prospective treatment regimen as often as the dominant frequency is determined.

10. The apparatus for pain treatment according to claim 6 wherein the computation means further operative calculate a prospective treatment regimen by summing the dominant frequency and a frequency offset value.

11. The apparatus for pain treatment according to claim 6 wherein the computation means is further operative to provide updated frequency stimulation signal at least each time the calculated prospective treatment frequency has changed from a previous value.

12. The apparatus for pain treatment according to claim 6 wherein the calculated prospective treatment frequency is not feedback in an amplified form to said leads via the amplifier.

13. The apparatus for pain treatment according to claim 6 wherein the calculated prospective treatment frequency is feedback in an amplified form to said leads via the amplifier.

* * * * *